United States Patent
Wong et al.

(10) Patent No.: US 6,423,762 B1
(45) Date of Patent: Jul. 23, 2002

(54) DENTURE ADHESIVE COMPOSITIONS COMPRISING A POLYMERIC ACTIVATOR

(75) Inventors: Eddie Wong, New Providence; Hal C. Clarke, Woodbridge; Robert C. Gasman, Montville; Joseph D. Synodis, Summit; Alfred J. Smetana, Wayne, all of NJ (US)

(73) Assignee: Block Drug Company, Inc., Jersey City, NJ (US)

( * ) Notice: Subject to any disclaimer, the term of this patent is extended or adjusted under 35 U.S.C. 154(b) by 0 days.

(21) Appl. No.: 09/480,210

(22) Filed: Jan. 10, 2000

Related U.S. Application Data

(63) Continuation of application No. 09/407,649, filed on Sep. 28, 1999, now Pat. No. 6,110,989, which is a continuation-in-part of application No. 09/163,698, filed on Sep. 30, 1998, now abandoned.

(51) Int. Cl.$^7$ ................................................. A61K 6/00
(52) U.S. Cl. ........................................................ 523/120
(58) Field of Search ........................................... 523/120

(56) References Cited

U.S. PATENT DOCUMENTS

| | | | |
|---|---|---|---|
| 3,868,432 A | 2/1975 | Keegan et al. ............... | 523/120 |
| 4,373,036 A | 2/1983 | Chang et al. ................ | 523/120 |
| 4,521,551 A | 6/1985 | Chang et al. ................ | 523/120 |
| 4,758,630 A | 7/1988 | Shah et al. .................. | 523/120 |
| 5,006,571 A | 4/1991 | Kumar et al. ................ | 523/120 |
| 5,093,387 A | 3/1992 | Schobel et al. ............. | 523/120 |
| 5,525,652 A | 6/1996 | Clarke et al. ................ | 523/120 |
| 5,543,443 A * | 8/1996 | Rajaiah et al. .............. | 523/120 |
| 5,658,586 A * | 8/1997 | Rajaiah et al. .............. | 523/120 |
| 5,830,933 A | 11/1998 | Synodis et al. ............. | 523/120 |
| 6,110,989 A * | 8/2000 | Clarke ........................ | 523/120 |

FOREIGN PATENT DOCUMENTS

| | | |
|---|---|---|
| WO | WO98/58619 | 12/1998 |

\* cited by examiner

*Primary Examiner*—Peter Szekely
(74) *Attorney, Agent, or Firm*—Nora Stein-Fernandez

(57) ABSTRACT

A denture adhesive composition is disclosed and comprises a polymeric activator in an amount of up to about 3 percent by weight based on the total weight of the denture adhesive composition; wherein the activator is selected from the group consisting of: poly(meth)acrylic acid, poly acrylic acid, polyitaconic acid, polycitraconic acid, and a monovalent alkali metal cation salt thereof. This composition exhibits enhanced adhesive performance and reduces oozing and incidence of food occlusion.

18 Claims, No Drawings

DENTURE ADHESIVE COMPOSITIONS COMPRISING A POLYMERIC ACTIVATOR

CROSS-REFERENCE TO RELATED APPLICATIONS

This is a continuation-in-part of application Ser. No. 09/407,649, filed Sep. 28, 1999, now U.S. Pat. No. 6,110.989, which is a continuation-in-part of application Ser. No. 09/163,698, filed Sep. 30, 1998, now abandoned.

BACKGROUND OF THE INVENTION

1. Field of the Invention

The present invention relates to denture adhesives containing a polymeric activator, such as a polymeric acid, and to methods of improving a denture adhesive product by adding a polymeric activator.

2. Description of the Related Art

Dentures are substitutes for missing teeth and serve as replacement for all or some of the teeth found in the oral cavity. Despite diligent efforts by dental professionals and designers of dental prostheses, dentures do not always fit perfectly. Over time, even well-fitting dentures can become ill-fitting due to natural shrinkage and changes in the gum or mucous tissues. Therefore, adherent creams, liquids, powders or liners are often used to secure dentures within the mouth.

There are a number of desirable characteristics of a denture fixative composition. One extremely desirable attribute is that it develops a high degree of adhesion to the oral mucosa upon contact with saliva so that the dentures can be held in place as soon as they are seated in the mouth. It is also highly desirable that the mucilage be spread over the denture-mucosa interface in order to effectively seal the denture in place and that the mucilages possess sufficient adhesive strength to withstand the stresses of mastication which act to rupture the seal and thus dislodge the denture. The denture fixative must also exhibit sufficient resistance to degradation under the extreme environmental changes that occur in the oral cavity during such common actions as drinking coffee or other hot beverages. Of course, the adhesive must also be releasable so that the denture wearer may remove the dentures for cleaning and maintenance. Denture adhesives are generally sold as a cream, liner or strip, liquid or powder, and many examples are well known in the art.

Early denture adhesives contained finely ground particles of natural gums that expanded when wet with water to become a viscous gel, which acted as a cushion and an adherent between the denture plate and the gum tissue. These denture adhesives, however, have tended to be supplanted by synthetic polymeric denture adhesives.

U.S. Pat. No. 3,003,988, for example, describes a dental fixative composition in which the dental fixative is a mixed partial salt containing calcium cations and alkali or quaternary ammonium cations of a lower alkyl vinyl ether-maleic anhydride type copolymer. The mixed salt copolymer is stated to be a water-insoluble, but water sensitized, copolymer.

U.S. Pat. No. 3,736,274 teaches a dental fixative composition that contains a lower alkyl vinyl ether-maleic anhydride polymeric material, a polymeric N-vinyl lactam and a sodium carboxymethyl cellulose. The carboxymethyl cellulose prevents the lower alkyl vinyl ether-maleic anhydride copolymer-N-vinyl lactam complex from completely precipitating when placed in water. U.S. Pat. No. 3,868,432 teaches an anhydrous denture adhesive composition that is a mixture of a copolymer of an acrylamide and an anionic synthetic gum component which can be a copolymer of maleic acid with vinyl lower alkyl ether.

Numerous pharmaceutical formulations have employed polyacrylic acid and the use thereof has, in the past, been primarily directed to the exploitation of its thickening, suspending and emulsifying capabilities when the polymer is partially or wholly neutralized with an inorganic base, water soluble amine or some combination thereof. In aqueous systems, the partially or wholly neutralized polyacrylic acid generates a gel which has low cohesive strength with a structure that may be easily ruptured when it is subjected to stresses such as those that occur during mastication.

U.S. Pat. No. 4,373,036 discloses a denture fixative composition containing a combination of hydroxypropyl cellulose and another material which can be a partially neutralized, optionally crosslinked, polyacrylic acid. In the examples of the patent, the other material is always more than 20% of the combination.

U.S. Pat. No. 4,521,551 discloses a denture fixative composition containing denture fixative excipients and as the denture fixative, a water soluble partially neutralized alkyl vinyl ether-maleic acid or anhydride copolymer, optionally partly crosslinked with a polyhydroxyl compound, and at least one hydrophilic polymer, preferably sodium carboxymethyl cellulose, polyethylene oxide or hydroxy propyl sugar.

U.S. Pat. No. 4,758,630 discloses denture adhesives comprising zinc and strontium partial salts of lower alkyl vinyl ether-maleic acid copolymers, wherein the zinc and strontium cations are unmixed with any other cations or ester functions in the copolymeric salt, the remaining initial carboxyl group being unreacted.

U.S. Pat. No. 5,006,571 discloses denture adhesives comprising a substantially anhydrous mixture of a mixed Na/Ca salt of methyl vinyl ether-maleic acid, sodium carboxymethyl cellulose, and a trivalent cation. Dihydroxy aluminum sodium carbonate may be the source of the trivalent cation, in which case a food grade acid must be added to aid in release of the aluminum from the composition. Exemplary acids include citric acid, malic acid, tartaric acid, and fumaric acid. The acid may comprise up to about 4 percent by weight of the denture adhesive composition. Additionally, benzoic acid or sorbic acid may be included in the denture adhesive as a preservative.

U.S. Pat. Nos. 5,525,652 and 5,830,933 disclose the use of mixed copolymer acid salts in the formulation of denture adhesive compositions. Preferably the salts are mixed salts of Ca/Na or Ca/K, and most preferably they are partial Zn/Mg salts and Na/Zn/Mg salts. U.S. Pat. No. 5,093,387 also discloses that benzoic acid and sorbic acid may be used as preservatives in denture adhesive formulations in amount of about 0.03 to about 0.6 percent by weight of the total denture adhesive composition.

Each of the denture adhesive materials discussed above has certain advantages and disadvantages when compared with other denture adhesives. The search for better denture adhesive materials continues, however, and denture adhesives with better hold, longer hold and better organoleptic properties, i.e., enhanced adhesive performance and reduced oozing and incidence of food occlusion, are always desirable. In our earlier PCT patent application, WO09858619, it was believed that the activator had to be a polymer activator containing repeating units which contained at least seven carbon atoms in total and at least four carbon atoms in the backbone as well as being a carboxylic acid or alkali metal salt thereof. Certain other polymeric acids and their partial salts were found not to work in the context of the invention, e.g., alginic acid (or a salt thereof) also known as polymannuronic acid and sodium carboxymethyl cellulose. We then concluded that non-chelating polyacrylic acids, such as the Carbopols, would not be expected to work. To our surprise, we discovered that polyacrylic acids, as well as polymethacrylic, polycitraconic acid, and polyitaconic acids, do in fact function as an activator in denture adhesives to provide better hold, longer hold and better organoleptic properties.

SUMMARY OF THE INVENTION

The present invention provides a denture adhesive composition comprising a polymeric activator in an amount of up to about 3 wt. % based on the total weight of the denture adhesive composition, wherein the activator is selected from the group consisting of: poly(meth)acrylic acid, poly acrylic acid, polyitaconic acid, polycitraconic acid, and a monovalent alkali metal cation salt thereof.

The present invention further provides a method of preparing a denture adhesive composition comprising: preparing a mixture that comprises a polymeric activator in an amount of up to about 3 percent by weight based on the total weight of the denture adhesive composition, wherein the activator is selected from the group consisting of: poly (meth)acrylic acid, poly acrylic acid, polyitaconic acid, polycitraconic acid, and a monovalent alkali metal cation salt thereof, forming a denture adhesive composition including said mixture; and recovering said denture adhesive composition.

DETAILED DESCRIPTION OF THE INVENTION

A novel denture adhesive base composition with surprisingly good performance has been discovered. Specifically, denture adhesives of the present invention reduce oozing, enhance adhesive performance, reduce the incidence of food occlusion and provide greater consumer confidence of product function.

Denture Fixative Component

While any known denture adhesive can be employed, the preferred denture adhesive employed in the composition is a partial salt of a copolymer of maleic acid and a lower alkyl vinyl ether. Preferably, the alkyl group has from about 1 to about 5 carbon atoms, but a more preferable copolymer includes methyl vinyl ether. As is known by those skilled in the art, the molecular weight of such copolymers can affect the properties of the copolymer and, by extension, the denture adhesive comprising the copolymer. Polymers generally do not have one precise molecular weight. Rather, polymers are made up of many polymer molecules, each having a different molecular weight. One way to estimate the viscosity average molecular weight of a polymer is to measure its specific viscosity under specified conditions. The preferred copolymer of the invention generally has a specific viscosity (measured as a 1% weight/volume solution in methyl ethyl ketone at 25° C.) of at least about 1.5. More preferably, the specific viscosity is at least about 2.5.

The preferred copolymer of the invention is generally used as its partial salt. The maleic anhydride group must be hydrolyzed to form the corresponding dicarboxylic acid which can, in turn, react with metal compounds that partially neutralize the carboxylic acid groups on the copolymer.

Preferably less than 100% of the carboxylic acid groups on the copolymer chain are neutralized. More preferably, the metal compounds neutralize from about 50% to about 90% of the carboxylic acid groups of the copolymer and most preferably from about 65% to about 75% of the carboxylic acid groups. The preferred alkaline cations include sodium, zinc, potassium, calcium, iron (II), strontium, magnesium and the zirconium oxy cation. Preferably the salts are single or mixed partial salts of calcium, sodium, potassium, magnesium, zinc, iron (II), strontium and the zirconium oxy cation. Preferred mixed partial salts of two cations include calcium/sodium, calcium/magnesium, zinc/magnesium, calcium/zinc, sodium/zinc, potassium/zinc, sodium/ magnesium, potassium/magnesium or calcium/potassium salts, and most preferably they are partial calcium/zinc and/or zinc/magnesium salts. Preferred mixed salts of three cations include calcium/sodium/zinc and sodium/zinc/ magnesium salts. A further description of the preferred adhesives can be found in the aforementioned U.S. Pat. Nos. 5,525,652 and 5,830,933. In general, the adhesive active material will be about 15–60%, preferably about 25–55% of the composition.

Activator

The polycarboxylic acid activators used in the present invention have the repeat units shown in the following formulas:

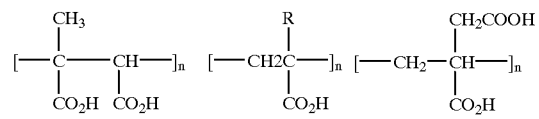

The polyacrylic acids have molecular weights of about 500,000 to about 5,000,000, preferably about 2,000,000 to 4,000,000 and most preferably about 3,000,000. The polymethacrylic acids have a repeat unit of $-CH_2-CH(CH_3)$ (COOH)$-$. The polyitaconic acids have a repeat unit of $-CH_2-CH(COOH)(CH_2COOH)-$. The polycitraconic acids have a repeat unit of $-CH_3-C(COOH)-CH$ (COOH)$-$. Preferred salt cations for the activators include nontoxic monovalent alkali metal cations, preferably sodium or potassium cations.

In one embodiment, this present invention provides a denture adhesive composition comprising a polymeric activator in an amount of up to about 3% by weight based on the total weight of the denture adhesive composition. Preferably, the polymeric acid is present in an amount of about 0.1 percent to about 2 percent by weight, and more preferably about 1 percent by weight. In the absence of the polymeric activator of this invention, compositions may be prepared that do not exhibit the enhanced effect achieved from the composition of the claimed invention. The denture adhesives of the invention only exhibit the improved effect upon addition of free polymeric activator.

In a preferred embodiment of the invention, the denture adhesive composition comprises the Mg/Zn/Na or Ca/Na or Ca/Zn partial salt of a lower alkyl vinyl ether-maleic acid and polyacrylic acid (or salt), wherein the polyacrylic acid (or partial alkali metal salt) is present in an amount of up to about 3 percent by weight based on the total weight of the denture adhesive composition. More preferably, the polyacrylic acid (or salt) is present in an amount of about 0.1 percent to about 2 percent, and most preferably about 1 percent by weight based on the total weight of the denture adhesive composition.

Other Components—Cellulosic Polymers

The dental adhesive compositions of the present invention may further comprise a water-soluble cellulosic polymer as is known in the art such as methyl cellulose, polyethyl-2- oxazoline, polyethylene oxide, carboxymethyl cellulose, sodium carboxymethyl cellulose, hydroxyethyl cellulose, polyvinyl pyrrolidone, and the like. The cellulosic polymer, preferably sodium carboxymethyl cellulose, is a powder which when moistened, becomes hydrated and tacky or gunmmy thereby providing additional adhesive functionality to the dental adhesive composition. The carboxymethyl cellulose gums are water-soluble, anionic long chain polymers whose properties vary to some extent depending on the number of carboxymethyl groups that are substituted per anhydroglucose unit in each cellulose molecule. These cellulose polymers comprise from about 15% to about 35%, and preferably from about 17% to about 28% of the dental adhesive composition.

Other Components—Excipients

The compositions contain a denture fixative together with an excipient. Typical excipients include waxes and oils. The oils useful in the invention include without limitation mineral oil, propylene glycol, polyethylene glycol, vegetable oils such as corn, soybean, cottonseed, castor, palm and coconut oils and animal oil such as fish oil. In general, amounts of oil of about 1% to about 30% by weight of the total denture adhesive composition are usable, with amounts of about 10% to about 25% being preferred.

When a mineral oil vehicle is employed, polyethylene may be optionally used as a gelling agent to provide a hydrocarbon thickener vehicle, and thus is used to adjust the extrusion properties of the finished denture adhesive composition. Polyisobutylene may also be used in conjunction with polyethylene to further enhance the viscosity properties of the vehicle.

Alternatively, a stock petrolatum, with or without mineral oil, may be employed depending on the specific handling qualities that are desired in the final product. A particularly preferred combination involves use of petrolatum in amounts of about 10% to about 40%, and a light or heavy mineral oil in amounts of about 5% to about 30% by weight of the denture adhesive composition in order to have an easily extrudable formulation having a cream-like consistency. A more preferred combination involves use of petrolatum in amounts of about 20% to about 30%, and a light or heavy mineral oil in amounts of about 10% to about 20% by weight of the denture adhesive composition.

Waxes may be added to the petrolatum, either during preparation of the denture adhesive or to form a petrolatum premix. Such waxes may be natural or synthetic waxes including, without limitation, microcrystalline waxes. When used, amounts of generally about 1% to about 25% by weight of the total denture adhesive composition are usable, with amounts of about 10% to about 25% being preferred.

Other materials often included in denture adhesives include flavoring agents, sweetening agents, viscosity modifiers, coloring agents, preservatives and thickeners. Other water soluble polymers such as xanthan gum, polyethylene oxide, polyacrylamide, polyvinyl pyrrolidone (PVP), chitosan, polyvinyl alcohol, karaya gum, carboxymethyl cellulose, methyl cellulose, polyethyl-2-oxazoline, sodium alginate, hydroxyethyl cellulose and hydroxy propyl cellulose may also form part of the final denture adhesive formulation. Vehicles such as petrolatum, mineral oil, vegetable oil, propylene glycol and the like may form part of cream-type formulations, and non-toxic anti-caking agents such as silica, talc, dicalcium phosphate anhydrous and the like can be present. The compositions can also contain, if desired, other known denture fixatives.

The denture adhesive compositions may also be used as a denture adhesive and/or bioadhesive and comprise one or more therapeutic actives suitable for mucosal or topical administration such as anesthetic, analgesic, antibiotic, anti-inflammatory, antibacterial, antimicrobial, antifungal, aromatic, antihistamine, benzaldehyde, insulin, steroid, dentinal desensitizing, anti-neoplastic, agents, and mixtures thereof. The phrase "suitable for mucosal or topical administration", as used herein, describes agents which are pharmacologically active when absorbed through internal mucosal surfaces of the body such as the oral cavity, or applied to the surfaces of the skin. Therapeutic actives may be present at a level of from about 0% to about 70%, by weight of the composition.

Therapeutic actives that are useful in these compositions include antimicrobial agents such as iodine, sulfonamides, bisbiguanides or phenolics; antibiotics such as tetracycline, neomycin, kanamycin, metronidazole or clindamycin; anti-inflammatory agents such as aspirin, acetaminophen, naproxen and its salts, ibuprofen, ketorolac, fluorbiprofen, indomethacin, eugenol or hydrocortisone; dentinal desensitizing agents such as potassium nitrate, strontium chloride or sodium fluoride; anesthetic agents such as lidocaine or benzocaine; antifungals; aromatics such as camphor, eucalyptus oil, and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

The compositions of the present invention may also include one or more components which provide flavor, fragrance, and/or sensate benefit. Suitable components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxyamide agents such as N-ethyl-p-menthane-3-carboximide which is described in U.S. Pat. No. 4,136,163. These agents may be present at a level from about 0% to about 10% by weight of the composition.

The colorants useful in the present invention include pigments such as titanium dioxide, and may also include various dyes suitable for food, drug and cosmetic applications, also known as D&C dyes. Two preferred colorants are D&C Red No. 7 and D&C Red No. 30.

Hydrophilic or hydrophobic fumed silica can also be used as a thickener for the adhesive. A fine white powder, fumed silica is the micronized form of silica (silicon dioxide, $SiO_2$) made by the combustion of silicon tetrachloride in a hydrogen-oxygen furnace. The amount of fumed silica used in the composition may range from about 0.7% to about 3.5%. Precipitated or colloidal silica may also be used.

Preparation

The denture adhesive compositions of this invention may be in the form of pastes, powders, liquids, creams, or liners, such that when in contact with saliva, the denture adhesive compositions of the present invention hydrate and develop a high degree of tack and uniform viscous mucilages of high cohesive strength and that, when spread over the denture-mucosa interface, provide superior denture stabilizing properties.

The method for preparing the denture adhesive compositions may be conveniently carried out by mixing the components until a homogeneous mixture is obtained and recovering the resulting product. Preferably, the base composition is prepared as a preblended formulation that can be mixed with the remaining components used to prepare the final formulation. Mixing is conveniently performed at temperatures suitable to melt the components to be blended. For example, if polyethylene and mineral oil are to be employed, such materials may be heated to temperatures from about 90° C. to 95° C., and are preferably cooled prior to blending with other components such as the polymeric acid and coloring agents.

Optionally, the adhesive base composition to which the polymeric activator is added comprises a mixed partial salt of a chelating polymer acid. More preferably, the adhesive is a mixture comprising either a triple salt such as a Mg/Zn/Na lower alkyl vinyl ether-maleic acid partial salt or the Ca/Na or the Ca/Zn partial salt of a lower alkyl vinyl ether-maleic acid mixed salt, carboxymethyl cellulose, and an activator acid (or monovalent alkali metal cation salt) in which the activator acid or salt is present in an amount of up to about 3 wt. %.

EXAMPLES

In order to further illustrate the present invention, various illustrative examples are set forth below to provide denture adhesives with better, longer hold and better organoleptic properties. In these examples, as well as throughout the specification and claims, all parts and percentages are by weight and all temperatures in °C. unless otherwise specified.

Example 1

This example demonstrates the preparation of a denture adhesive formulation according to this invention. A cream type denture adhesive was prepared by blending together in a Hobart type mixer the following:

| Component | Units (wt. %) |
|---|---|
| Mineral oil, heavy | 16.00% |
| Petrolatum | 27.85% |
| Fumed Silica | 0.50% |
| Mixed partial Mg/Zn/Na salt of MVE/MA (GANTREZ ® salt) | 29.45% |
| Sodium Carboxymethyl Cellulose | 23.55% |
| Spray Dried Peppermint | 0.80% |
| Red No. 7 Lake | 0.02% |
| Spray Dried Spearmint | 0.80% |
| Red No. 30 Lake | 0.03% |
| CARBOPOL ® 974P | 1.00% |
| Total | 100.00% |

The fumed silica is added to a hot dispersion of the petrolatum in mineral oil. Next the GANTREZ® salt is slowly added to the mix, followed by the sodium carboxymethyl cellulose. Once the GANTREZ® salt and the sodium carboxymethyl cellulose have been thoroughly blended in, the dyes are added followed by the polyacrylic acid (CARBOPOL® 974P). The adhesive is next mixed for 25 additional minutes and then it is cooled to room temperature and discharged.

The mixed partial salt is prepared as follows. 900.40 grams of room temperature purified water were charged into a main reaction kettle equipped with a high speed stirrer. 76.26 grams of anhydrous MVE/MA copolymer were added to the main mix kettle, with continuous mixing. 250.11 grams of purified room temperature water were charged into a secondary kettle, and 3.91 grams of NaOH; 15.89 grams of ZnO and 3.94 grams of MgO were added slowly. All inorganic materials used as ingredients in the examples herein are NF or USP grade anhydrous raw materials, unless otherwise noted. The contents of the secondary kettle were well mixed to form a homogeneous slurry. This slurry was added into the main reaction kettle while mixing, then the temperature of the reaction was raised to 85–90° C. and held at that temperature for two hours. The resulting dispersion was poured into shallow stainless steel drying trays, and the trays were placed in a hot air convection oven at 70° C., for 18–20 hours to give a dried salt. Although trays were used in this example, a drum drier would also be acceptable.

The dried Mg/Zn/Na Gantrez salt was then milled through a suitable mill and screened through a #100 mesh sieve. A one percent solution of the resulting powder would have a pH of from about 5 to about 7. This salt is a 10% Na/ 40% Zn/ 20% Mg salt of MVE/MA copolymer.

Example 2
(Comparative)

A cream adhesive is prepared exactly as shown in example 1, except that the CARBOPOL® addition is omitted.

When tested, the denture adhesive formulations prepared according to Example 1 provided improved adhesive performance over the denture adhesive formulation of Example 2.

Example 3

A cream adhesive is prepared as shown in Example 1 except that the amount of CARBOPOL® was reduced to 0.5% and the amount of Petrolatum was increased by 0.5%.

Examples 4–5

The cream adhesive of Example 1 is prepared except that a partial sodium or potassium CARBOPOL® salt is used in place of the CARBOPOL®.

Example 6

A powder type adhesive is prepared by mixing 49.5 grams of the GANTREZ® salt of Example 1, 49.5 grams of sodium carboxymethyl cellulose and 1 gram of CARBOPOL® 947P together in a ribbon blender.

While specific examples of materials, compositions and processes have been described and illustrated, it will be apparent to those skilled in the art that a wide variety of changes and modifications may be made and still be within the broadest aspects of this invention. It should be understood that the examples and the particular proportions and methods of procedure set forth are intended to be illustrative only.

What is claimed is:

1. A denture adhesive composition comprising a denture adhesive effective amount of a denture adhesive polymer salt and a pharmacologically acceptable carrier therefor and an amount of an activator not exceeding about 3 percent by weight based on the total weight of the denture adhesive composition, wherein the activator is selected from the group consisting of: poly(meth)acrylic acid, poly acrylic acid, polyitaconic acid, polycitraconic acid, and a monovalent alkali metal cation salt thereof.

2. The denture adhesive composition of claim 1, wherein said activator is present in an amount of about 0.1 percent to about 2 percent by weight based on the total weight of the denture adhesive composition.

3. The denture adhesive composition of claim 1, wherein said polymeric activator is polyacrylic acid.

4. The denture adhesive composition of claim 1, wherein said polymeric activator is polymethacrylic acid.

5. The denture adhesive composition of claim 1, wherein said polymeric activator is polyitaconic acid.

6. The denture adhesive composition of claim 1, wherein said polymeric activator is polycitraconic acid.

7. The denture adhesive composition of claim 1, in which the denture adhesive salt is a mixed partial sat of a copolymer of maleic acid and an alkyl vinyl ether and at least one cation, wherein all of said cations are selected from the group consisting of sodium, strontium, iron (II), potassium, calcium, magnesium, zinc and the zirconium oxy cations.

8. The denture adhesive composition of claim 7, wherein one of said cations is a sodium cation and the alkyl moiety is methyl.

9. The denture adhesive composition of claim 1, further comprising at least one member selected from the group consisting of: therapeutic actives suitable for mucosal or topical administration, natural or artificial sweetening agents, menthol, menthyl lactate, wintergreen oil, peppermint oil, spearmint oil, leaf alcohol, 3-1-menthozypropane, 1,2-diol, paramenthane carboxyamides, and mixtures thereof.

10. The denture adhesive of claim 9, wherein the therapeutic actives are selected from the group consisting of anesthetic, analgesic, antibiotic, anti-inflammatory antibacterial, antimicrobial, antifungal, aromatic, antihistamine, benzaldehyde, insulin, steroid, dentinal desensitizing, anti-neoplastic, agents, and mixtures thereof.

11. A method of preparing a denture adhesive composition comprising:

(a) preparing a mixture which comprises an activator in an amount not exceeding about 3 percent by weight based on the total weight of the denture adhesive composition, wherein the activator is selected from the group consisting of poly(meth)acrylic acid, poly acrylic acid, polyitaconic acid, polycitraconic acid, and a monovalent alkali metal cation salt thereof;

(b) forming a denture adhesive composition including said mixture; and (c) recovering said denture adhesive composition.

12. The method of claim 11, wherein said activator is present in an amount of about 0.1 percent to about 2 percent by weight based on the total weight of the denture adhesive composition.

13. The method of claim 11, in which the denture adhesive polymer salt is a mixed partial salt of a copolymer of maleic acid and an alkyl vinyl ether. wherein the cations of said salt comprise zinc and magnesium ions.

14. The method of claim 13, wherein said cations further comprise zinc ions and the alkyl moiety is methyl.

15. The method of claim 11, wherein said polymeric activator is polymethacrylic acid.

16. The method of claim 11, wherein said polymeric activator is polyitaconic acid.

17. The method of claim 11, wherein said polymeric activator is poly acrylic acid.

18. The method of claim 11, wherein said polymeric activator is polycitraconic acid.

* * * * *